United States Patent [19]
Bovy et al.

[11] Patent Number: 6,037,365
[45] Date of Patent: Mar. 14, 2000

[54] AMINOBENZAMIDINOSUCCINYL LACTONE DERIVATIVES USEFUL AS INHIBITORS OF PLATELET AGGREGATION

[75] Inventors: Philippe Roger Bovy, Mareil Marly, France; Joseph Gerace Rico; Thomas Edward Rogers, both of Ballwin, Mo.

[73] Assignee: G.D. Searle & Co., Skokie, Ill.

[21] Appl. No.: 09/160,089

[22] Filed: Sep. 25, 1998

[51] Int. Cl.$^7$ ........................ A61K 31/34; C07D 305/12
[52] U.S. Cl. ........................ 514/471; 514/365; 514/457; 514/465; 548/204; 549/288; 549/320; 549/321
[58] Field of Search ........................ 549/288, 216, 549/283, 320, 321; 548/204; 514/450, 471, 365, 457, 465

[56] References Cited

U.S. PATENT DOCUMENTS

| | | | |
|---|---|---|---|
| 4,517,686 | 5/1985 | Ruoslahti | 3/1 |
| 4,578,079 | 3/1986 | Ruoslahti | 623/11 |
| 4,589,881 | 5/1986 | Pierschbacher | 623/11 |
| 4,614,517 | 9/1986 | Ruoslahti | 623/11 |
| 4,661,111 | 4/1987 | Ruoslahti | 623/11 |
| 4,997,667 | 3/1991 | Nofre | 426/548 |
| 5,039,805 | 8/1991 | Alig | 546/224 |
| 5,084,466 | 1/1992 | Alig | 514/353 |
| 5,100,875 | 3/1992 | Marguerie | 514/18 |
| 5,220,050 | 6/1993 | Bovy | 514/357 |
| 5,270,319 | 12/1993 | Belliotti | 514/269 |
| 5,344,957 | 9/1994 | Bovy | 560/35 |
| 5,597,825 | 1/1997 | Himmelsbach | 514/255 |

FOREIGN PATENT DOCUMENTS

| | | |
|---|---|---|
| 2037153 | 9/1991 | Canada . |
| 275 748 | 7/1988 | European Pat. Off. . |
| 298 820 | 1/1989 | European Pat. Off. . |
| 372 486 | 6/1990 | European Pat. Off. . |
| 381 033 | 8/1990 | European Pat. Off. . |
| 445 796 | 9/1991 | European Pat. Off. . |
| 496 378 | 7/1992 | European Pat. Off. . |
| 502 536 | 9/1992 | European Pat. Off. . |
| 539 343 | 4/1993 | European Pat. Off. . |
| 542 708 | 5/1993 | European Pat. Off. . |
| 93/12074 | 6/1993 | WIPO . |
| 93/12103 | 6/1993 | WIPO . |
| 93/18058 | 9/1993 | WIPO . |
| 94/00424 | 1/1994 | WIPO . |
| 94/22820 | 10/1994 | WIPO . |
| 95/06038 | 3/1995 | WIPO . |

OTHER PUBLICATIONS

M. Taddei et al., "Electrophilic Hydroxylation with Bis(trimethylsilyl) peroxxide", Synthesis, No. 8, pp. 633–635 (1986).

E.C. Horning et al., eds., Org. Synth., coll. vol. 3, John Wiley & Sons, New York, pp. 140–141 (1955).

J.R. Luly et al., "A Synthesis of Protected Aminoalkyl Epoxides from α–Amino Acids", J. Org. Chem., vol. 52, pp. 1487–1492 (1987).

S.G. Davies et al., "Asymmetric Synthesis of R–β–Amino Butanoic Acid and S–β–Tyrosine: Homochiral Lithium Amide Equivalents for Michael Additions to α,β–Unsaturated Esters", Tetrahedron: Asymmetry, vol. 2, No. 3, pp. 183–186 (1991).

R.T. Boere et al., "Preparation of N, N, N'–tris(trimethylsilyl)amidines; a conventient route to unsubstituted amidines", J. Organomet. Chem., vol. 331, pp. 161–167 (1987).

W.E. Parham et al., "Aromatic Organolithium Reagents Bearing Eelctrophilic Groups", Acct. Chem. Res., vol. 15, pp. 300–305 (1982).

D.M. Haverstick et al., "Inhibition of Platelet Adhesion to Fibronectin, Fibrinogen, and von Willebrand Factor Substrates by a Synthetic Tetrapeptide Derived From the Cell–binding domain of Fibronectin", Blood, vol. 66, No. 4, pp. 946–952 (1985).

E. Ruoslahti et al., "New Perspectives in Cell Adhesion: RGD and Integrins", Science, vol. 238, pp. 491–497 (1987).

J.A. Zablocki et al., "Potent in Vitro and in Vivo Inhibitors of Platelet Aggregation Based Upon the Arg–Gly–Asp Sequence of Fibrinogen", J. Med. Chem., vol. 38, pp. 2378–2394 (1995).

C. F. Stanfield et al., "Preparation of Protected Amino Aldehydes", J. Org. Chem., vol. 46, pp. 4797–4789 (1981).

M. Kloczewiak et al., "Platelet Receptor Recognition Site on Human Fibrinogen", Biochem., vol. 23, No. 8, pp. 1767–1774 (1984).

E.F. Plow et al., "The effect of Arg–Gly–Asp–containing peptides on fibrinogen and von Willebrand factor binding to platelets", Proc. Nat'l Acad. Sci., vol. 82, No. 23, pp. 8057–8061 (1985).

Z.M. Ruggeri et al., "Inhibition of platelet function with synthetic peptides designed to be high–affinity antagonists of fibrinogen binding to platelets", Proc. Nat'l Acad. Sci., vol. 83, No. 15, pp. 5708–5712 (1986).

M. Ginsberg et al., "Inhibition of Fibronectin Binding to Platelets by Proteolytic Fragments and Synthetic Peptides Which Support Fibroblast Adhesion", J. Biol. Chem., vol. 260, No. 7, pp. 3931–3936 (1985).

*Primary Examiner*—Amelia Owens
*Attorney, Agent, or Firm*—Fitzpatrick, Cella, Harper & Scinto

[57] ABSTRACT

This invention provides a compound of the formula

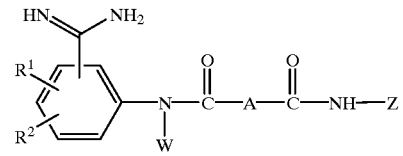

or a pharmaceutically acceptable salt thereof. The invention also provides pharmaceutical compositions of such compounds and a method of treatment to inhibit aggregation of platelets.

15 Claims, No Drawings

AMINOBENZAMIDINOSUCCINYL LACTONE DERIVATIVES USEFUL AS INHIBITORS OF PLATELET AGGREGATION

BACKGROUND OF THE INVENTION

1. Field of the Invention

This invention is directed to novel substituted aminobenzamidinosuccinyl lactone derivatives which inhibit aggregation of platelets. This invention is also directed to a pharmaceutical composition comprising these compounds. This invention is further directed to a method for inhibiting platelet aggregation.

2. Related Background Art

Platelets are cellular components of the blood responsible for coagulation and clot formation. Fibrinogen is a glycoprotein which binds to platelets in the coagulation mechanism. When a blood vessel receives an injury, platelets initially form a monolayer adhering to collagen in the underlying subendothelial matrix. The adherence of the platelets leads to their activation according to a process in which GP IIb-IIa receptors (a membrane glycoprotein) undergo a conformational change to allow for fibrinogen binding. The platelets then bind fibrinogen, which fibrinogen then adheres to additional platelets, forming a thrombus. At the same time, factor Xa mediates the cleavage of prothrombin to thrombin. Thrombin cleaves fibrinogen to fibrin, which forms a stable clot. Naturally occurring plasmin eventually cleaves fibrin and dissolves the clot. Inhibitors of different steps in this pathway are effective in modulating or preventing thrombus formation and/or clotting.

It is also known that fibronectin, a large glycoprotein and a major extracellular matrix protein, also interacts with fibrinogen and fibrin, as well as with other structural molecules such as actin, collagen, and proteoglycans. It has been found that relatively large peptide fragments found in fibronectin's cell-binding domain have cell-binding activity. See U.S. Pat. Nos. 4,517,686; 4,589,881; and 4,661,111. Additionally, short peptide fragments of the same molecule have been found to have cell-binding activity, or activity inhibiting cell-binding when placed in solution or suspension, presumably because they bind to the cell and prevent its binding to the substrate. See U.S. Pat. Nos. 4,578,079 and 4,614,517. Other synthetic peptides have also been used to inhibit binding of fibrinogen to platelets. See, e.g., Koczewiak et al., *Biochem.* 23:1767–1774 (1984); Plow et al., *Proc. Nat'l Acad. Sci.* 82:8057–8061 (1985); Ruggeri et al., *Proc. Nat'l Acad. Sci.* 83:5708–5712 (1986); Ginsberg et al., *J. Biol. Chem.* 260:3931–3936 35 (1985); Haverstick et al., *Blood* 66:946–952 (1985); Ruoslahti and Pierschbacher, *Science* 238:491–497 (1987); U.S. Pat. No. 5,344,957; European Patent Application 275,748; and European Patent Application 298,820.

Compounds containing an amidino group attached to an aromatic ring are also known to have cell-binding activity.

European Patent Application 496,378 discloses amidinobiphenyl compounds which inhibit cell-cell and cell-matrix interaction and are thus useful for treating thrombosis, cerebrovascular diseases, pulmonary embolisms, myocardial infarction, arteriosclerosis, osteoporosis, and tumor metastases.

European Patent Application 445,796 discloses amidinosubstituted acetic acid derivatives which have inhibitory action on the bonding of adhesive proteins to platelets as well as on platelet aggregation and cell-cell adhesion.

European Patent Application 372,486 discloses N-acyl β-amino acid derivatives and their salts. These compounds are said to be useful for inhibiting platelet aggregation in the treatment of thrombosis, stroke, myocardial infarction, inflammation, arteriosclerosis, and metastasis.

European Patent Application 381,033 discloses amidinoaryl or guanidinoaryl substituted alkanoic acid derivatives useful for the treatment of thrombosis, apoplexy, cardiac infarction, inflammation, arteriosclerosis, and tumors.

PCT Application WO 95/06038 discloses cyclic ureas substituted by an amidinophenyl group and a β-amino acid. These compounds are useful as platelet aggregation inhibitors.

PCT Applications WO 93/18058 and WO 95/06038, and European Patent Applications EP 542,708 and EP 539,343 disclose amidinobenzenaminosuccinyl acid derivatives useful as platelet aggregation inhibitors.

PCT Applications WO 94/00424, WO 93/12074 and WO 93/12103 disclose phenylamidine alkanoic acids and lactones useful as platelet aggregation inhibitors.

PCT Application WO 94/22820 discloses amidinophenyl pyrrolidinones, piperidinones, and azetidinones useful as platelet aggregation inhibitors.

U.S. Pat. Nos. 5,220,050 and 5,344,957 disclose amidinophenyl-substituted β-amino acid derivatives which are useful as platelet aggregation inhibitors.

J.A. Zablocki et al., J. Med. Chem., 38, 2378–2394 (1995) and European Patent Application No. 502,536, disclose aminobenzamidino succinyl compounds which are useful as platelet aggregation inhibitors.

The present invention is directed to novel aminobenzamidinosuccinyl lactones which inhibit platelet aggregation.

SUMMARY OF THE INVENTION

In accordance with the present invention, novel substituted aminobenzamidinosuccinyl lactones are provided which modulate and/or inhibit platelet aggregation. These compounds are represented by the general formula I:

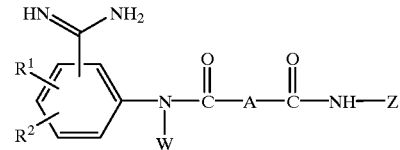

or a pharmaceutically acceptable salt thereof, wherein $R^1$ and $R^2$ are independently selected from the group consisting of hydrogen, halo, alkoxy, alkyl and hydroxy;

W is selected from the group consisting of hydrogen, alkyl, alkenyl, aryl or alkoxycarbonyl any of which may be substituted by alkyl, aryl or substituted aryl wherein each aryl substituent is selected from halo, alkoxy and alkyl;

A is selected from the group consisting of alkyl radicals, alkenyl radicals, alkynyl radicals, and alicyclic radicals, wherein each of said radicals may be optionally substituted with hydroxyl, alkoxy, alkyl, halo, aryl, or substituted aryl, wherein the aryl substituent is selected from the group consisting of halo, nitro, alkoxy and alkyl;

Z is a lactone structure which is represented by the formula:

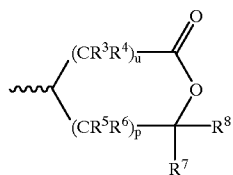

wherein $R^3$ and $R^4$ are independently selected from the group consisting of hydrogen, halo, alkoxy, alkyl and hydroxy;

$R^5$, $R^6$, $R^7$ and $R^8$ are independently selected from the group consisting of hydrogen, alkoxy, alkyl, alkenyl, alkyl sulfonyl, aryl sulfonyl; phosphate, phosphinate, phosphonate, each of which is attached through phosphorus and may be substituted on one or more of its oxygen atoms by alkyl, aryl, alkenyl or hydrogen; heterocyclic, phenyl, and substituted phenyl wherein each phenyl substituent is selected from halo, alkoxy, and alkyl;

u is an integer from 1 to 2;

p is an integer from 0 to 2; or

Z is a lactone which is fused to a benzene ring and represented by the formula

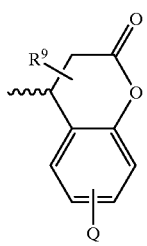

wherein Q is one or more substituents of the benzene ring (which may be in any available substituent positions) and are selected from the group consisting of hydrogen, halo, hydroxy, alkyl and alkoxy and $R^9$ is selected from the group consisting of hydrogen, halo, carboxyl, alkoxycarbonyl, alkyl or alkoxy.

This invention is also directed to a novel pharmaceutical composition comprising compounds of the formula I useful in inhibiting or modulating platelet aggregation or the like, particularly in inhibiting or modulating platelet aggregation by administrating an amount between 0.5 mg/kg to 10 mg/kg, preferably 3 mg/kg, to an animal in need thereof.

This invention is further directed to a method to therapeutically inhibit or modulate platelet aggregation or the like in a mammal in need of such treatment comprising a compound of the formula I in unit dosage form.

Many other objects and purposes of the invention will be clear from the following detailed description of the invention.

DETAILED DESCRIPTION OF THE INVENTION

The following terms used herein to describe substituent groups are defined as follows, unless otherwise indicated. The term "alkyl" refers to a straight or branched alkyl group containing from 1 to 8 carbon atoms. The term "alkenyl" refers to a straight or branched hydrocarbon group containing from 1 to 8 carbon atoms and at least one carbon-carbon double bond. The term "alkynyl" refers to a straight or branched hydrocarbon group containing from 1 to 8 carbon atoms and at least one carbon-carbon triple bond. The term "alicyclic" refers to a non-aromatic cyclic alkyl, cyclic alkenyl or cyclic alkynyl group containing up to 10 carbon atoms. The term "cycloalkyl" refers to a cyclic alkyl group containing up to 8 carbon atoms. The term "alkoxy" refers to an oxygen substituent substituted by alkyl. The term "alkoxycarbonyl" refers to a carbonyl substituent substituted by alkoxy. The term "aryl" refers to a group derived from a cyclic aromatic compound having up to 12 carbon atoms and which may be unsubstituted or substituted by alkyl, halo, alkoxy, trifluoromethyl, hydroxy, nitro, cyano, amino, dialkylamino or carboxyl groups. The term "aralkyl" refers to an alkyl substituent substituted by an aryl group. The term "heterocyclic" refers to a group derived from a monocyclic or fused bicyclic compound having no more than 10 ring atoms among which are from 1 to 4 atoms selected from nitrogen, oxygen and sulfur, and which may be unsubstituted or substituted by alkyl, halo, alkoxy, cyano, hydroxy, nitro, trifluoromethyl, amino, dialkylamino or carboxyl groups. The term "halo" refers to the substituent formed by covalent attachment of fluorine, chlorine, bromine, or iodine. The term "DMF" refers to N,N-dimethylformamide. The term "THF" refers to tetrahydrofuran.

The term "pharmaceutically acceptable salt" refers to a salt resulting from contact between a compound of this invention and an acid or base whose counter-ion is generally considered suitable for human consumption. A pharmaceutically acceptable salt comprises an ion derived from a compound of this invention, together with a counter-ion derived from an acid or base. Pharmaceutically acceptable salts derived from acids include such counter-ions as, for example, chloride, bromide, iodide, sulfate, phosphate, acetate, propionate, lactate, maleate, oxalate, malate, succinate, tartrate, and citrate. All of these salts may be prepared by conventional means by reacting, for example, the corresponding acid with a compound of this invention. Pharmaceutically acceptable salts derived from bases include such counter-ions as, for example, aluminum, calcium, lithium, magnesium, potassium, sodium, zinc, and organic cations derived from N,N'-dibenzylethylenediamine, chloroprocaine, choline, diethanolamine, ethylenediamine, meglumine (N-methylglucamine), and procaine.

The compounds of the present invention are set forth in previously defined Formula I. A preferred embodiment of the present invention is a compound represented by formula II:

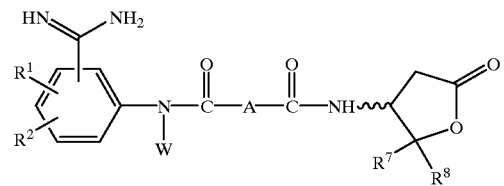

wherein $R^1$–$R^2$, $R^7$–$R^8$, W and A are the same as defined for Formula I.

A further preferred embodiment of the present invention is a compound represented by formula III:

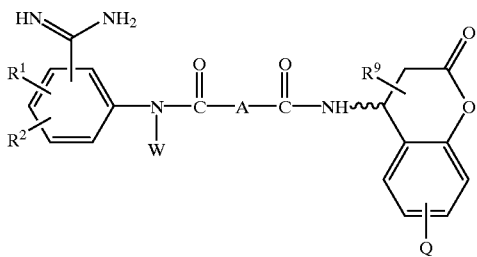

wherein $R^1$, $R^2$, $R^9$, W, A and Q are the same as defined for Formula I.

The compounds of this invention are useful in inhibiting platelet aggregation, for example, in treatment of thrombosis, stroke, myocardial infarction, inflammation, arteriosclerosis, and metastasis.

As previously noted, the compositions of this invention may be employed in a pharmaceutical composition for inhibiting or modulating platelet aggregation. In addition, this invention is also directed to a method of therapeutically inhibiting or modulating platelet aggregation in an animal in need thereof by administering thereto a unit dosage amount of the compounds of this invention.

The total daily dose of the compounds of this invention administered to a host in single or divided doses may be in amounts, for example, from 0.001 to 100 mg/kg body weight daily and more usually 0.01 to 10 mg/kg. Dosage Unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjutants and vehicles as desired.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic monoglycerides or diglycerides. In addition, fatty acids such as oleic acid find use in injectable preparations.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants such as wetting agents, emulsifying and suspending agents, and sweetening, flavoring, and perfuming agents.

While the compounds of the invention can be administered as the sole active pharmaceutical agent, they can also be used in combination with one or more active pharmaceutical ascots. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compounds in this invention can exist in various isomeric forms and all such isomeric forms are meant to be included. Tautomeric forms are also included in the invention. Pharmaceutically acceptable salts of such isomers and tautomers are meant to be included as well.

The compounds listed above may be prepared by standard synthetic methods combined with methods analogous to solution phase peptide synthesis, as described in "The Peptides: Analysis, Synthesis, Biology", E. Gross and J. Meienhofer, eds., vols. 1–5, Academic Press, New York, the disclosure of which is hereby incorporated by reference.

Six general synthetic sequences which outline preferred methods for preparation of the compounds of this invention are outlined in the following Schemes 1–6.

SCHEME 1

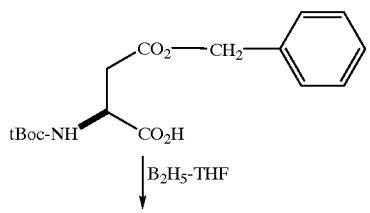

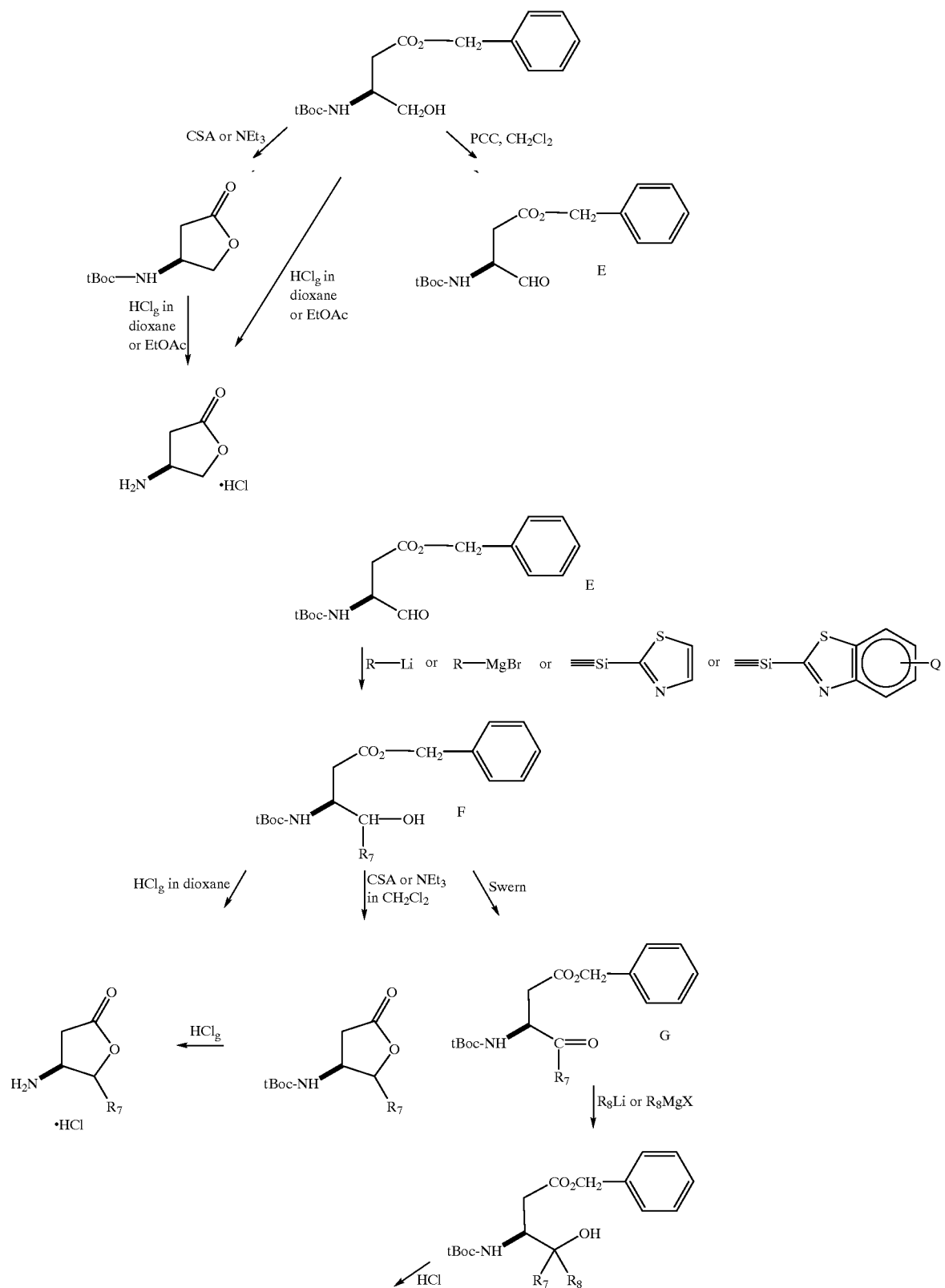

-continued

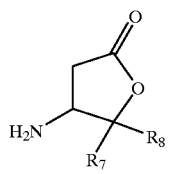

wherein R may be alkyl, phenyl or substituted phenyl, pyridyl, thienyl.

Scheme 1 describes the synthesis of the lactone (3-(S)-amino-5-oxo-furane) from the corresponding protected (L)-aspartic acid (N-tBoc-aspartic acid, a-benzyl ester). First, the protected amino acid was converted to the intermediate optically active alcohol using the borane-THF reagent (C. Stanfield et al., J. Org. Chem, 4797–89, 46, 1981). The alcohol ester is then lactonized using acid (camphor sulfonic acid or trifluoroacetic acid) or base (triethylamine) catalysis in an inert solvent such as, for example, dichloromethane or dioxane. The free lactone was then obtained as its hydrochloride salt from the action of dry hydrochloric acid in a solvent such as THF or dioxane. The enantiomeric lactone can be obtained by using the same procedure in the D-amino acid series. Ring substituted lactones can be obtained by, first, converting the intermediate protected alcohol to the corresponding aldehyde using an oxidation reaction such as, the Swern oxidation (J. R. Luly, J. F. Dellaria, J. J. Plattner, J. L. Soderquist and N. Yi, J. Org. Chem, 52, 1487–1492, 1987) or pyridinium chlorochromate in an aprotic solvent such as dichloromethane or pyridine. Nucleophilic addition of an anion to the aldehyde produces the substituted alcohol which is then cyclized and deprotected as before. Further oxidation of alcohol intermediate F by, for example, Swern oxidation would give substituted ketone G that could be lactonized as before, producing the $R_7$, $R_8$ disubstituted lactone.

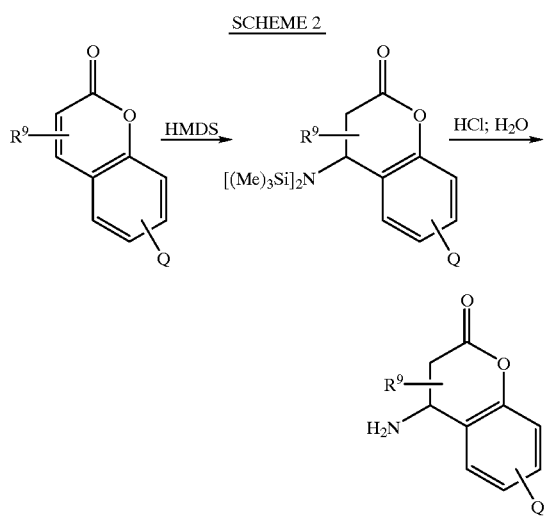

SCHEME 2

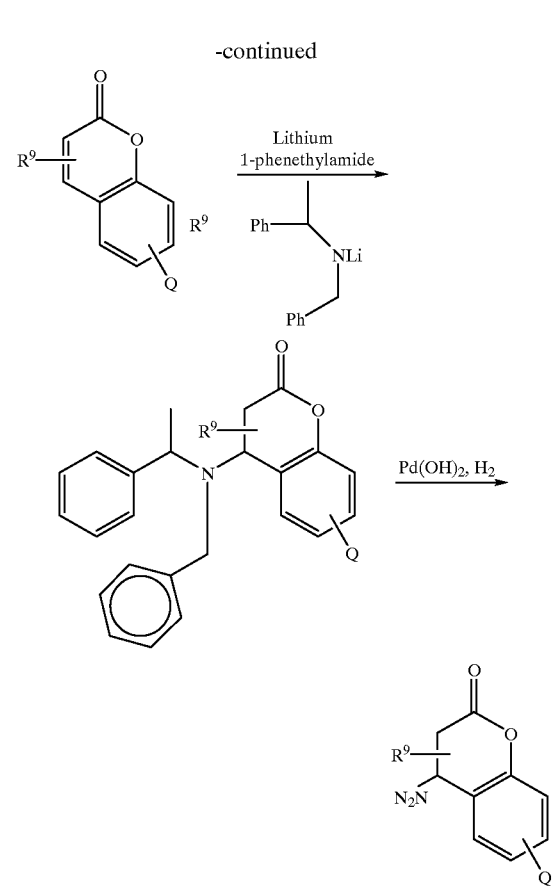

wherein Q and $R^9$ have the values listed in Formula I.

Scheme 2 outlines methods for preparing bicyclic lactones. The addition of lithium amide reagents to the coumarin nucleus affords through a Michael addition a protected form of 4-amino-3,4-dihydro-2-oxo-2H-1-benzopyrene. Examples of lithium amide reagents that can be used in that reaction are lithium examethyldisilazane or lithium benzylamide. When the enzylamide used is homochiral, a chiral bicyclic lactone could be obtained (S. G. Davies and O. Ichihara, Tetrahedron: Asymmetry, 2, 183–86, 1991). The free 4-amino-3,4-dihydro-2-oxo-2H-1-benzopyrane is obtained by a suitable deprotection procedure, e.g., aqueous acid for the silyl groups and hydrogenolysis in the presence of Pd(OH)$_2$ for the benzyl group or another method as described by T. H. Greene in "Protective Groups in Organic Synthesis", Wiley-Interscience (1980).

SCHEME 3

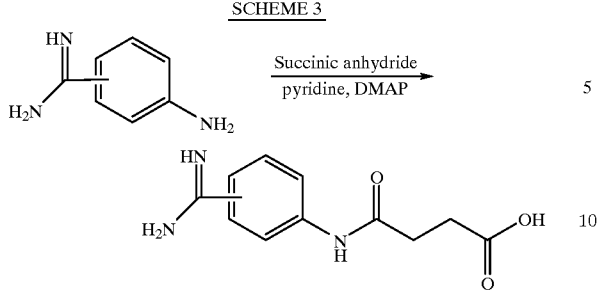

In Scheme 3, the aminobenzamidine is coupled to an alkanoic, alkenoic (both substituted or not) or alkynoic diacid. An activated form of the diacid is preferentially used. These activated forms include anhydrides, internal anhydride, acid chloride or one of the various activated forms as described in Principles of Peptide Synthesis, Bodansky, 1984, Springer-Verlag. A highly preferred procedure involves the condensation of an anhydride (e.g., succinic anhydride) with a salt of amino benzamidine. The reaction is best conducted in a polar solvent such as methylene chloride, acetonitrile, dioxane, dimethylformamide, dimethylsulfoxide or a mixture of such solvents in the presence of an acid binding agent such as sodium, potassium or cesium carbonate, triethylamine, pyridine, sodium hydride, dimethylaminopyridine, diazabicycloundecene, or a mixture of such agents, at temperatures ranging between 0° C. and 120° C.

a. Activated diacid b. $H_2S$, pyridine; MeI, acetone; $NH_4OAc$ or hexamethyl disilazane in diethyl ether.

A has the values described in formula I.

Alternatively, an aminobenzonitrile can be condensed with the desired diacid or diacid derivative as shown in Scheme 4. In that case, the nitrile can be converted to the amidine directly or at a later stage. When the aminobenzonitrile is used in the condensation reaction, the cyano group of the resulting intermediate is converted to the amidine via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI).

Alternatively, the nitrile can be converted to the amidine by the use of lithium bis(trimethylsilyl)amide in an inert solvent such as diethyl ether (R. T. Boeré et al, J. Organomet. Chem., 331, 161–67, 1987).

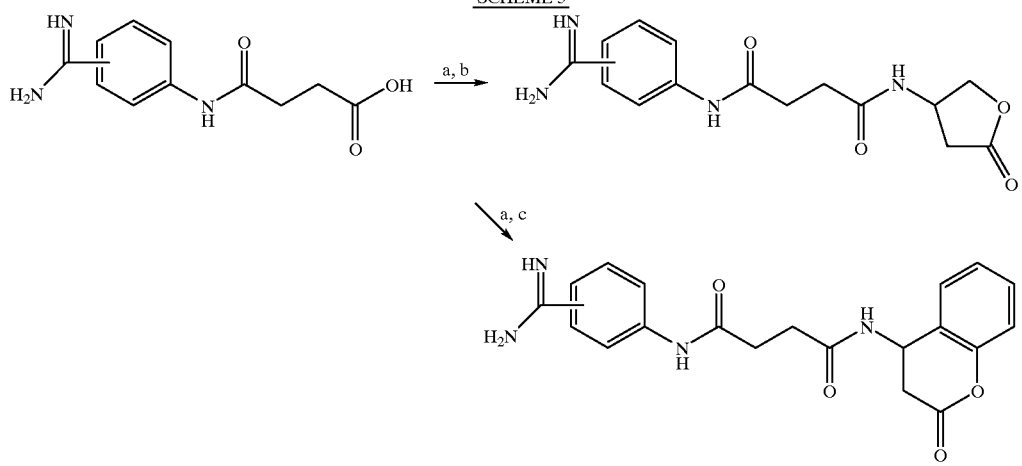

SCHEME 4 a. -ButOCOCl,NMM
b. γ-lactone
c. δ-lactone

The compounds of this invention may be prepared by coupling an amidine derivative (Schemes 3 and 4) with an amino lactone (Schemes 1 and 2) as illustrated in Scheme 5. The amide bonds may be formed using standard coupling reagents, e.g. dicyclohexylcarbodiimide (DCC), carbonyldiimidazole, disuccinimidyl carbonate (DSC), benzotriazole-1-yl-oxy-tris-(dimethylamino)-phosphonium hexafluorophosphate (BOP) or isobutyl chloroformate (mixed anhydride method).

Scheme 6 describes the preparation of derivatives of formula I using the amino nitrites as starting materials. The cyano group is kept intact as a precursor for the amidine function throughout two amide bond forming steps. The first nitrile intermediate is directly engaged in a reaction with the desired amino lactone. The fully elaborated nitrile intermediate is then converted to the benzamidine. A method of choice to produce the amidine function is via the thiomidate procedure as described in Scheme 4.

SCHEME 6

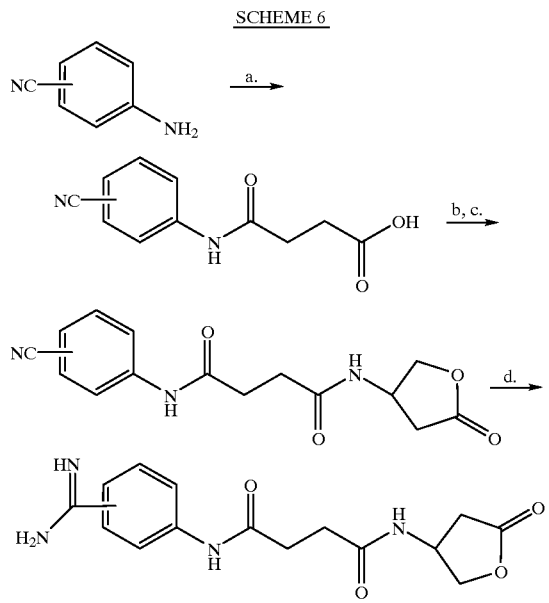

a. Succinic anhydride, pyridine, DMAP
b. Mixed anhydride, NMM
c. Lactone derivative
d. $H_2S$, pyridine, MeI, acetone; $HN_4OAc$ The $R_1$, $R_2$ substituents, (where $R_1$ and $R_2$ are chosen from hydrogen or halogen, or an alkyl radical or alkoxy radical) can be introduced at the aminobenzonitrile stage. The phenyl group can be halogenated using bromine, iodine, or chlorine. The alkyl group can be introduced by low temperature lithium halogen exchange followed by quenching with the appropriate aldehyde, as described by W. E. Parham and C. K. Bradsher, *Acct. Chem. Res.* 300, 1982, the disclosure of which is hereby incorporated by reference. The resulting alcohol can be converted to alkyl by hydrogenolysis, as described in Reductions in Organic Chemistry, M. Hudicky, ed., John Wiley & Sons, New York, 1984, the disclosure of which is hereby incorporated by reference. Where $R_1$ or $R_2$ is hydroxy or alkoxy, such substituents can be introduced by low temperature lithium halogen exchange followed by quenching with electrophilic bis (trimethylsilyl) peroxide [(TMSO)2], as described by M. Taddei and A. Ricci, *Synthesis* 633–635, 1986, the disclosure of which is hereby incorporated by reference, which affords the silyl ether. The silyl ether can be converted to the hydroxy derivative by treatment with hydrochloric acid, as also described by M. Taddei and A. Ricci. The hydroxy in the presence of a weak base ($K_2CO_3$) and an appropriate alkyl halide, $R_8$-Hal, as disclosed by C. F. Allen and J. W. Gates, Org. Synth. Coll., vol. 2 3 140, 1955, the disclosure of which is hereby incorporated by reference, will form the ester as well. The ester can be selectively cleaved in the presence of the ether with one equivalent of sodium hydroxide.

Substituted aminonitrile can be used to prepare substituted N-aminobenzamidine succinyl derivatives as specifically illustrated in Scheme 7 for the chloro derivative.

SCHEME 7

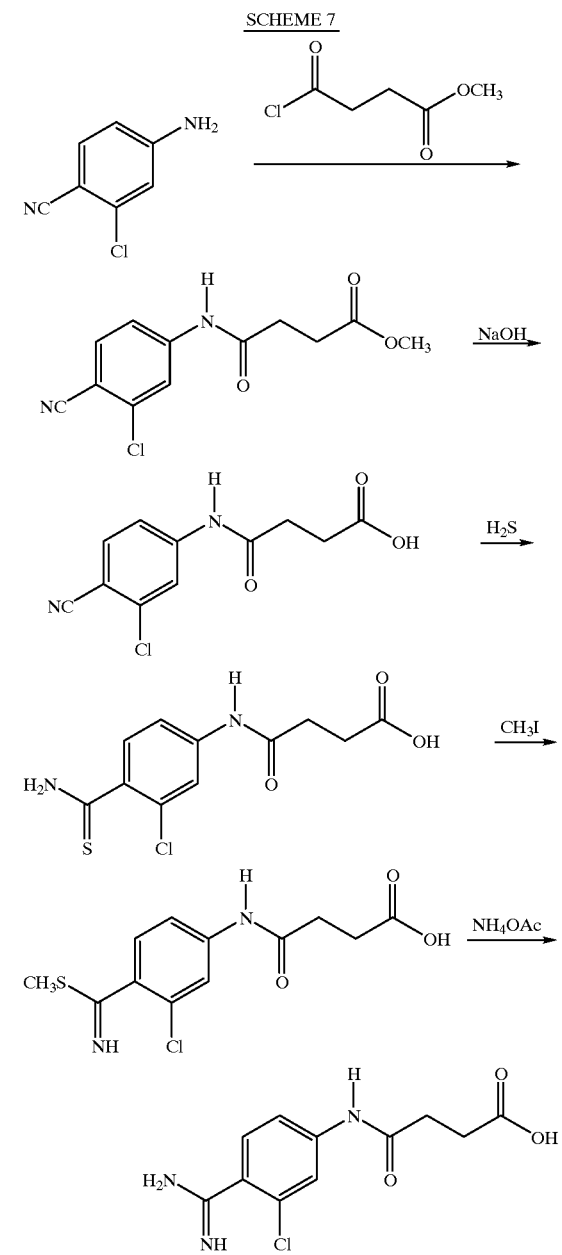

The derivative where W is different from hydrogen can be obtained by using an appropriately substituted aminobenzamidine. For example, the 4-methylaminobenzamidine can be reacted with succinic anhydride in a manner similar to the amino benzamidine.

Purification of final compounds is usually by reverse phase high performance liquid chromatography (see High Performance Liquid Chromatography Protein and Peptide Chemistry, F. Lottspeich, A. Henscher, and K. P. Hupe, eds., Walter DeGruyter, New York, 1981) or crystallization.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

N-[4-(aminoiminomethyl)phenyl]-N'-(tetrahydro-5-oxo-3S-furanyl)butanediamide, Trifluoroacetate

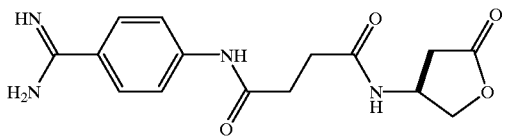

Step 1. Preparation of 3-N-tBoc-amino-4-hydroxy-(3S)-butyric acid benzyl ester

N-tBoc-L-aspartic acid, β-benzyl ester (10.0 mmole) was dissolved in 10 mL of tetrahydrofuran (THF) and added dropwise over a period of 30 min to a 0° C. solution of BH$_3$-THF (20 mL, 20.0 mmole), under argon. After the mixture was stirred for an additional 1–2 hr at 0° C., the reaction was quenched by dropwise addition of 10% acetic acid in methanol and the solvent evaporated. The oil residue was dissolved in ethyl acetate and extracted with 1N HCl, water, and 1M NH$_4$HCO$_3$. The ethyl acetate layer was dried (Na$_2$SO$_4$) and volatiles evaporated to give an oil that could be crystallized from isopropanol/hexane (mp 56–57° C.): $^1$H NMR (CDCl$_3$) δ 1.45 (s, 9H), 2.65 (d, 2H), 3.68 (d, 2H), 5.12 (s, 2H), 5.25 (m, 1H), 7.35 (m, 5H).

Step 2. Preparation of N-tBoc-3-amino-5-oxo-3S-furane.

The 3-N-tBoc-amino-4-hydroxy-butyric acid benzyl ester (20 g, 64 mmole) was stirred in 200 mL dichloromethane at room temperature for 16 hr in the presence of a catalytic amount of camphor sulfonic acid. Solvent was removed in vacuo and the crude product purified by flash chromatography (Merck 60 silica gel, ethyl acetate/hexane/1% triethylamine). The N-tBoc-3-aminolactone was isolated as a white solid (5.4 g).

Step 3. Preparation of 3-amino-5-oxo-3S-furane.

The 3-N-tBoc aminolactone (5.0 g, 25 mmole) isolated in Step 2 was dissolved in 20 mL 4N HCl/dioxane. After 45 minutes at 25° C., 10 mL of 4N HCl/dioxane was added and after 1 hr the excess HCl was removed in vacuo. The resulting solution deposited white crystals upon standing. These were filtered and dried to give 2.9 g of the desired product as the hydrochloride salt; $^1$H NMR (d$_6$ DMSO) δ 2.55 (dd, 1H, J$_1$=18.3 Hz, J$_2$=2.5 Hz), 3.0 (dd, 1H, J$_1$=8.5 Hz, J$_2$=18.3 Hz), 4.1 (m, 1H), 4.35 (dd, 1H, J$_1$=10.5 Hz, J$_2$=2.7 Hz), 4.5 (dd, 1H, J$_1$=10.5 Hz, J$_2$=6.5 Hz); MS (FAB) 102.1 (M+H).

Step 4. Preparation of N-[4-aminoiminomethyl)phenyl]-N'-(tetrahydro-5-oxo-3S-furanyl)butanediamide, trifluoroacetate.

To a flame-dried flask under argon atmosphere, 4-[[4-(aminoiminomethyl)phenyl]-amino]-4-oxobutanoic acid hydrochloride (ABAS) (2 g, 7.4 mmole) prepared in Example 11 was added to dry dimethylformamide (DMF) (70 mL) followed by N-methyl morpholine (NMM) (0.74 g, 7.4 mmole) and isobutyl chloroformate (10 g, 7.3 mmole) at 5° C. The mixture was stirred for 5 minutes. To this was added the 3-amino lactone hydrochloride (1.02 g) prepared in Step 3, followed by N-methyl morpholine (0.75 g, 74. mmole) and the reaction allowed to warm to room temperature. After several hours the solvent was removed at 55° C. under reduced pressure and the product purified by preparative reverse phase high pressure liquid chromatography (RPHPLC) and lyophilized to give 1.0 g of the title compound (white solid): $^1$H NMR (d$_6$ DMSO) δ 2.3 (m, 4H), 2.55 (m, 2H), 2.82 (m, 1H), 4.0 (m, 1H), 4.38 (m, 2H), 7.77 (s, 4H), 8.47 (d, 1H, J=4.8 Hz), 8.74 (s, 2H), 9.13 (s, 1H), 10.39 (s, 1H). MS (FAB) 319.1 (M+H). Elemental analysis; Required for C$_{15}$H$_{18}$N$_4$O$_4$.C$_2$HF$_3$O$_2$.0.5 H$_2$O: C 46.26 H 4.57 N 12.69; Found: C 46.34 H 4.37 N 12.53

Step 5. Preparation of 3S-[[4-[[4-aminoiminomethyl) phenyl]amino]-1,4-dioxobutyl]amino]-4-hydroxybutanoic acid, trifluoroacetate

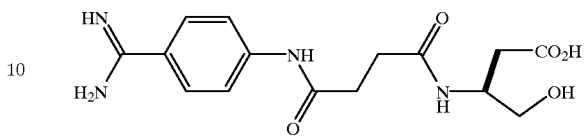

The lactone prepared in Example 1, Step 4 was dissolved in water (20 mL) and the pH adjusted to 10.5 by addition of LiOH.H$_2$O. The reaction was allowed to proceed at room temperature for 2 hours and the product isolated by RPHPLC. The appropriate fractions were adjusted to pH 7 by addition of LiOH prior to solvent removal. Subsequent lyophilization gave a white solid: $^1$H NMR (d$_6$ DMSO) δ 2.5 (m, 6H), 2.9 (m, 1H), 4.08 (m, 1H), 4.42 (M, 2H), 7.80 (s, 4H), 8.5 (d, 1H), 8.85 (s, 2H), 9.15 (s, 2H), 10.4 (s, 1H), MS (FAB) 337.1 (M+H), 319.2 (M-H$_2$O+H) . Elemental analysis; Required for C$_{15}$H$_{20}$N$_4$O$_5$.CF$_3$CO$_2$H.1.5 H$_2$O: C 42.77 H 5.07 N 11.75; Found: C 43.06 H 4.24 N 11.45

EXAMPLE 2

N-[4-(aminoiminomethyl)phenyl]-N'-(tetrahydro-5-oxo-2-phenyl-3S-furanyl)butanediamide, Trifluoroacetate (Isomer A)

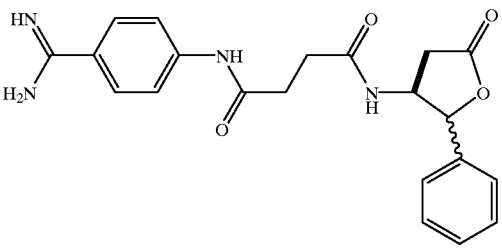

Step 1. Preparation of Phenyl lactone, hydrochloride.

The 3-N-tBoc-amino-4-hydroxy-butyric acid benzyl ester prepared in example 1, step 1 was oxidized to the corresponding aldehyde using the following Swern oxidation conditions: oxalyl chloride (6.40 g, 20.72 mmole) was dissolved in dry CH$_2$Cl$_2$ (25 mL) under argon and cooled to −63° C. using a dry ice/chloroform bath. Dry dimethylsulfoxide (DMSO) (? g, 41.4 mmole) dissolved in CH$_2$Cl$_2$ (12 mL) was added in a dropwise fashion over 15 minutes. The alcohol (6.40 g, 20.7 mmole), dissolved in methylene chloride (50 mL) was then added over 10 minutes. After stirring the reaction mixture for an additional 10 minutes, Et$_3$N (11.6 mL, 82.9 mmole, 4.0 eq.) in CH$_2$Cl$_2$ (25 mL) was added over 15 minutes. The resulting mixture was stirred for 15 minutes and quenched by addition of water (31 mL) to the well stirred mixture. The resulting slurry was poured onto hexanes (250 mL) and the organic layer washed with aqueous KHSO$_4$. The aqueous layer was extracted with diethyl ether and the combined organic extracts were washed with saturated NaHCO$_3$, dried (Na$_2$SO$_4$) and evaporated to give 5.8 g of a light yellow oil which was substantially the desired aldehyde. A small portion was purified by flash chromatography (hexane: ethyl acetate, Merck 60 silica gel): $^1$H NMR (300 MHz) (CDCl$_3$) δ 1.46 (s, 9H), 2.95 (m, 2H), 4.37 (m, 1H), 5.13 (s, 2H), 5.62 (m, 1H), 7.38 (m, 5H), 9.65 (s, 1H), MS (FAB+) 314.3 (M+Li).

Step 2. Preparation of 3-N-tBoc-amino-4-hydroxy-4-phenyl-(3S)-butyric acid benzyl ester.

To a diethyl ether (150 mL) solution of aldehyde (5.0 g, 15 mmole) prepared in Step 1 at −40° C. (acetonitrile/dry ice bath) was added in a dropwise fashion a 3.0M solution of phenyl magnesium bromide in diethyl ether (10.8 mL, 32.6 mmole, 2 eq). The resulting mixture was stirred for 15 minutes and warmed to room temperature. After several minutes the mixture was poured into 1M $K_2HPO_4$. The aqueous layer was extracted again with ether, the combined ether layers washed with aqueous $NaHCO_3$, dried ($Na_2SO_4$) and evaporated to give an oil (5.66 g) that was used without further purification: $^1H$ NMR (300 MHz) ($CDCl_3$) δ 1.4 (multiple singlets, 9H), 2.65 (m, 2H), 4.18 (m, 1H), 5.15 (m, 2H), 7.4 (m, 10H); MS (FAB+) 392.4 (M+Li+).

Step 3. Preparation of 2-phenyl-3-N-tBoc-amino-5-oxo-3S-furane.

The hydroxy-ester product of Step 2 (5.31 g, 13.8 mmol) was taken up in benzene (100 mL), a catalytic amount of camphor sulfonic acid was added, and the solution refluxed (Dean-Stark) for five hours. The solvent was then removed. Conversion to lactone was 50% so the reaction was reconstituted and refluxed for a further 6 hours. Solvent was removed and the resulting oil taken up in ethyl acetate. The organic layer was washed with aqueous saturated $NaHCO_3$ dried ($Na_2SO_4$) and evaporated to give a mixture of the desired diastereomeric lactones as a viscous oil in a 2:1 ratio and benzyl alcohol: $^1H$ NMR (300 MHz) ($CDCl_3$) δ 1.35, 1.45 (s, 2:1, 9H), 2.75 (m, 2H), 4.5, 4.75 (m, 2:1, 1H), 4.7 (s, 2H), 5.1 (m, 1H), 5.7 (d, 1H), 7.35 (m, 1OH); MS (FAB+) 284.6 (M+Li+).

Step 4. Preparation of 2-phenyl-3-amino-5-oxo-3S-furane, hydrochloride.

The lactone (0.94 g, 3.4 mmol) prepared in Step 3 was treated with 4N HCl in dioxane (20 mL) at room temperature until gas evolution ceased. Excess HCl was removed by evaporation and the desired amino lactone isolated as a white crystalline solid that was desiccated (0.48 g, 66%): $^1H$ NMR (300 MHz) ($d_6$ DMSO) δ 3.05 (m, 2H), 4.4 (m, 1H), 5.85 (d, 1H), 7.4 (s, 5H), 8.2 (bs, 3H); MS (FAB+) 178 (M+H+).

Step 5. Preparation of N-[4-(aminoiminomethyl)phenyl[-N'-(tetrahydro-5-oxo-2-phenyl-3S-furanyl)butanediamide), trifluoroacetate (Isomer A)

The reaction between ABAS (3.1 g, 11.5 mmole) and the aminophenyl lactone (1.63 g, 7.63 nmol) prepared in Step 4 was carried out in a fashion similar to Example 1, Step 5. Isolation of the diastereomers A (1.26 g) and B (0.19 g) was by preparative RPHPLC and subsequent lyophilization to give white solids: $^1H$ NMR (500 MHz), ($d_6$ DMSO) δ (Diastereomer A) 1.90 (m, 1H), 2.3 (m, 4H), 3.1 (m, 1H), 4.83 (m, 1H), 5.70 (d, 1H), 7.3 (m, 5H), 7.75 (m, 4H), 8.2 (d, 1H), 8.82 (bs, 2H), 9.15 (bs, 2H), 10.3 (s, 1H); MS (FAB+) 395.0 (M+H+). Elemental Analysis: Calculated for $C_{21}H_{22}N_4O_4.C_2F_3O_2H.0.5\ H_2O$: C 53.88 H 4.67 N 10.83; Found C 53.24 H 4.50 N 10.70

Step 6. Preparation of 3S-[[4-[[4-(aminoiminomethyl) phenyl]amino]-1,4dioxobutyl]amino]-4-hydroxy-phenyl-butanoic acid, trifluoroacetate The diastereoisomer prepared in step 5 was hydrolyzed to the corresponding hydroxy-acid using conditions of Example 1, step 5. NMR, MS and elemental analysis data were consistent with the desired structure.

EXAMPLE 3

N-[4-(aminoiminomethyl)phenyl]-N'-(tetrahydro-5-oxo-2-phenyl-3S-furanyl)butanediamide, trifluoroacetate (Isomer B)

Diastereoisomer B was obtained as described in step 5, Example 2 as a white powder (0.19 g): $^1H$ NMR (500 MHz), ($d_6$ DMSO) δ 2.55 (m, 5H), 2.95 (m, 1H), 4.38 (m, 1H), 5.35 (d, 1H), 7.36 (m, 5H), 7.78 (s, 4H), 8.60 (d, 1H), 8.85 (bs, 2H), 9.15 (bs, 2H), 10.4 (s, 1H); MS (FAB+) 395.0 (M+H+). Elemental Analysis: Calculated for $C_{21}H_{22}N_4O_4.C_2F_3O_2H.0.5\ H_2O$: C 53.38 H 4.67 N 10.83; Found: C 53.22 H 4.43 N 10.80

Step 2. Preparation of 3S-[[4-[[4-(aminoiminomethyl) phenyl]amino]-1,4-dioxobutyl]amino]-4-hydroxy-phenylbutanoic acid, trifluoroacetate The diastereoisomer isolated in Step 1 was hydrolyzed to the corresponding hydroxy-acid using conditions of Example 1, step 5. NMR, MS and elemental analysis data were consistent with the desired structure.

EXAMPLE 4

N-[4-(aminoiminomethyl)phenyl-N'-[2R(S)-4-fluorophenyl)tetrahydro-5-oxo-3S-furanyl] butanediamide, Trifluoroacetate (Diastereoisomer A)

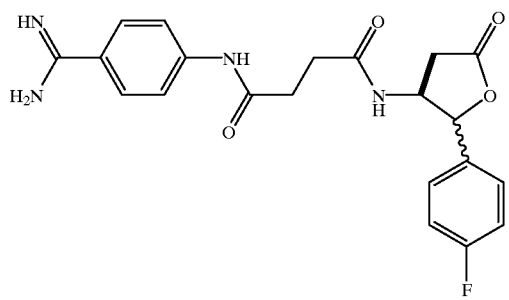

Step 1. 3-N-tBoc-amino-4-hydroxy-4-fluorophenyl-(3S)-butyric acid, benzyl ester.

The aldehyde (5.0 g, 16.3 mmole) prepared in Example 2, step 1 was reacted with 4-fluorophenyl magnesium bromide (16.3 mL of a 2.0M solution in diethyl ether, 32.6 mmole) in the same fashion as Example 2, step 2 to give the desired N-protected hydroxy-ester (6.0 g). MS (FAB) 410.1 (M+Li+).

Step 2. Preparation of N-tBoc-3-amino-(4-fluorophenyl) tetrahydro-5-oxo-3S-furane.

The Hydroxy-ester from step 1 was converted to the lactone (3.72 g) using the conditions of Example 2, step 3. MS (FAB) 302.1 ( M+Li+).

Step 3. Preparation of 3-amino-2-(4-fluorophenyl) tetrahydro-5-oxo-3S-furane, hydrochloride.

The lactone (3.72 g) produced in step 2 was deprotected as in Example 2, step 4 to give the desired amine hydrochloride salt as a tan solid (2.21 g). $^1H$ NMR, ($d_6$-DMSO+ TFA) δ 3.0 (m, 2H), 4.4 (m, 1H) 5.9 (d, 1H), 7.4 (m, 4H), 8.1 (bs, 3H).

Step 4. Preparation of N-[4-(aminoiminomethyl)phenyl]-N'-[2R(S)-(4-fluorophenyl)tetrahydro-5-oxo-3S-furanyl] butanediamide, trifluoroacetate The coupling between the amino-lactone prepared in step 3 and ABAS was achieved in a similar fashion to Example 2, step 5. Lyophilization of the two diastereomers A and B gave white solids (0.713 g Isomer A, 0.263 g Isomer B). $^1H$ NMR, ($d_6$ DMSO), δ, Isomer A; 2.45 (m, 1H), 2.8 (m, 5H), 3.65(m, 1H), 5.3 (m, 1H), 6.2 (d, 1H, J=5.5), 7.7 (m, 4H), 8.25 (m, 4H), 8.8 (d, 1H, J=8.7), 9.6 (bd, 4H), 10.8 (s, 1H); MS (FAB) 413.3 (M+H+). Elemental Analysis: Calculated for $C_{21}H_{21}FN_4O_4.C2F_3O_2.H_2O$: 50.69 H 4.41 N 10.29; Found: C 51.05 H 4.23 N 10.07

Step 5. Preparation of 3S-[[4-[[4-(aminoiminomethyl) phenyl]amino]-1,4-dioxobutyl]amino]-4-hydroxy-(4-fluoro-phenyl)butanoic acid, trifluoroacetate Hydrolysis of the lactone isolated in step 4 above was carried out as described in Example 1, step 5 to give the desired hydroxy-acid: MS (FAB) 431.2 (M+H+). Elemental Analysis: Calculated for $C_{21}H_{23}FN_4O_5.1.5\ F_3C_2O_2LiH_2O$: C 45.86 H 3.98 N 8.92; Found: C 45.75 H 4.17 N.8.82.

EXAMPLE 5

N-[4-(aminoiminomethyl)phenyl]-N'-[2R(S)-(4-fluorophenyl)tetrahydro-5-oxo-3S-furanyl] butanediamide, Trifluoroacetate (Diastereoisomer B)

Step 1. Isolation of N-[4-(aminoiminomethyl)phenyl]-N'-[2R(S)-(4-fluorophenyl)tetrahydro-5-oxo-3S-furanyl]-butanediamide, trifluoroacetate (Diastereoisomer B) was obtained as described in Example 4, step 4 as a white powder (0.236 g): $^1$H NMR, ($d_6$ DMSO), $\delta$ 2.6 (m, 6H), 3.0 (m, 1H), 4.4 (m, 1H), 5.35 (d, 1H), 7.39 (m, 4H), 7.8 (s, 4H), 8.6 (d, 1H), 8.8 (bs, 2H), 9.2 (bs, 2H), 10.4 (s, 1H). Elemental Analysis: Calculated for $C_{21}H_{21}FN_4O_4.C_2F_3O_2H.H_2O$: C 50.69 H 4.41 N 10.29; Found: C 50.67 H 4.03 N 10.00.

Step 2. Preparation of 3S-[[4-[[4-(aminoiminomethyl)-phenyl]amino]-1,4-]dioxobutyl]amino]-4-hydroxy-(4-fluoro-phenyl)butanoic acid, trifluoroacetate Hydrolysis of the lactone isolated in step 1 above was carried out as described in Example 1, Step 5 to give the desired hydroxy-acid: MS (FAB) 431.2 (M+H+). Elemental Analysis: Calculated for $C_{21}H_{23}FN_4O_5 1.5F_3C_2O_2Li\ H_2O$: C 45.86 H 3.98 N 8.92; Found: C 45.48 H 4.05 N 8.55.

EXAMPLE 6

N-[4-(aminoiminomethyl)phenyl]-N'-[tetrahydro-5-oxo-2-(2-thiazolyl)-3S-furanyl]butanediamide, Trifluoroacetate

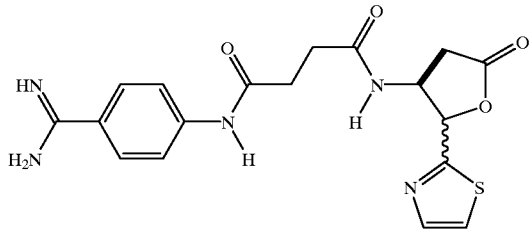

Step 1. Preparation of 3-N-tBoc-amino-4-trimethylsilyloxy-4-(thiazol-2-yl)-3S-butyric acid benzyl ester A solution of the aldehyde (8.6 g, 28 mmol) prepared in step 1, Example 4, in anhydrous dichloromethane was cooled at 0–5° C. in an ice bath. Trimethylsilyl thiazole (Fluka, 6.6 g, 42 nmol, 1.5 eq) was added dropwise via syringe. The reaction mixture was stirred at 5° C. for 30 min, and allowed to warm up to 25° C. After stirring for 1 hr, the solvent was removed in vacuo to leave a light orange oil (11.7 g): $^1$H NMR (300 MHz, $d_6$-DMSO) $\delta$ 0 (m, 6H), 0.35 (s, 3H), 1.35 (m, 9H), 2.4 (m, 2H), 4.35 (m, 1H), 5.0 (m, 3H), 7.2 (5H), 7.4 (m, 1H), 7.6 (m, 1H), 8.0 (m, 1H): MS (FAB) 471 (M+Li+).

Step 2. Preparation of 3-N-tBoc-amino-4-hydroxy-4-(thiazol-2-yl)-3S-butyric acid benzyl ester A solution of 10.7 g of the product prepared in step 1 in 100 mL THF, 10 mL water and 2 mL of a 1.0M solution of tetrabutylammonium fluoride in THF was stirred at room temperature for 1 hr. The solvent was removed in vacuo and the resulting alcohol used in the cyclization step without further purification: MS (FAB) 399 (M+Li+).

Step 3. Preparation of 3-N-tBoc-amino-2-(thiazol-2-yl)-5-oxo-3S-furane.

A solution of 8.9 g of the product prepared in step 2, in 200 mL benzene was refluxed with a Dean-Stark trap in the presence of a catalytic amount of camphorsulfonic acid. After 16 hr reflux, the reaction was concentrated in vacuo to an oil which was purified on a silica gel column (25% ethyl acetate in hexane containing 1% triethylamine). The lactone (1.4 g) was obtained as an oil: $^1$H NMR (DMSO-d6) $\delta$ 1.5 (m, 9H), 2.65 (m, 1H), 3.1 (m, 1H), 4.3 (m, 1H), 7.4 (d, 1H, J=3.2 Hz), 7.8 (d, J=3.2 Hz): MS (FAB) 291 (M+Li+).

Step 4. Preparation of 3-amino-2-(thiazol-2-yl)-5-oxo-3S-furane, hydrochloride.

A solution of 3-N-tBoc-amino-2-(thiazol-2-yl)-5-oxo-3S-furane (isolated in step 3) in 4N HCl in dioxane was stirred for two hours. The white crystalline solid which was isolated by filtration is a mixture of two diastereoisomers: MS (FAB) 184 (MH+).

Step 5. Preparation of N-[4-(aminoiminomethyl)phenyl]-N'-[tetrahydro-5-oxo-2-(2-thiazolyl)-3S-furanyl]-butanediamide, trifluoroacetate The coupling between the amino thiazole lactone prepared in step 4 and ABAS was achieved in a similar fashion to Example 2, step 5 to give a mixture of diastereomeric isomers. Lyophilization gave white solids. $^1$H NMR (300 MHz): $\delta$ 2.4 (m, 7H), 2.7 (m, 1H) 4.5 (m, 1H), 5.0 (m, 1H), 7.7 (m, 7H), 9.2 (m, 4H), 10.4 (s, 1H); MS (FAB) 420 (M+H+H$_2$O).

Step 6. Preparation of 3S-[[4-[[4-(aminoiminomethyl) phenyl]amino]-1,4-dioxobutyl]amino]-4-hydroxy-2-thiazolylbutanoic acid, trifluoroacetate Hydrolysis of the lactone prepared in step 5 was carried out as described in Example 2, step 6 using lithium hydroxide to give the desired hydroxy-acid lithium salt; MS(FAB) 420.2 (M+H+). Elemental Analysis: Calculated for $C_{18}H_{20}N_5O_5S\ Li.1.5\ F_3C_2O_2H.H_2O$: C 41.03 H 3.86 N 11.40; Found: C 41.06 H 3.52 N 11.18.

EXAMPLE 7

N-[4-(aminoiminomethyl)phenyl]-N'-[2-ethenyltetrahydro-5-oxo-3S-furanyl]butanediamide, Trifluoroacetate

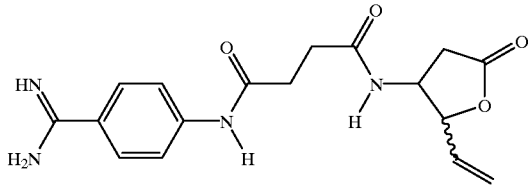

Step 1. Preparation of 3-N-t-Boc-amino-4-hydroxy-(3S)-5-hexenoic acid benzyl ester.

The aldehyde (9.5 g, 31 mmole in 200 mL diethyl ether) prepared in Example 2, step 1 was reacted with vinyl magnesium bromide (68 mL of a 1.0M solution in tetrahydrofuran, 50 mmole) in the same fashion as Example 2, step 2 to give the desired N-protected hydroxy-ester (9.43 g golden viscous oil). The desired N-t-Boc hydroxy benzyl ester was isolated by flash chromatography using hexane: ethyl acetate MS (FAB) 342.2 (M+Li+).

Step 2. Preparation of N-tBoc-3-amino-2-ethenyltetrahydro-5-oxo-3S-furane.

The hydroxy-ester from step 1 was converted to the lactone using the conditions of Example 2, step 3. Lactone (2.3 g) contaminated with benzyl alcohol was obtained by flash chromatography (silica gel; hexane: ethyl acetate gradient). $^1$H NMR (d$_6$-DMSO) δ 1.40 (s, 9H), 2.6 (m, 2H), 4.2 (m, 1H), 4.4 (m, 1H), 5.2 (m, 2H) 5.8 (m, 1H). MS (FAB) 243.2 (M+Li+).

Step 3. Preparation of 3-amino-2-ethenyl-tetrahydro-5-oxo-3S-furane.

The lactone (2.3 g) produced in step 2 was deprotected as in Example 2, step 4 to give the desired amine hydrochloride salt as a tan solid (hygroscopic) after trituration with diethyl ether (1.43 g). $^1$H NMR (d$_6$-DMSO) δ 3.0 (m, 2H), 4.1 (m, 1H), 4.4 (m, 1H), 5.3 (m, 2H), 6.0 (m, 1H), 8.8 (m, 3H).

Step 4. Preparation of N-[4-(aminoiminomethyl)phenyl]-N'-[2-ethenyl-tetrahydro-5-oxo-3S-furanyl]butanediamide, trifluoroacetate The coupling between the amino-vinyl lactone (0.7 g, 4.3 mmole) prepared in step 3 and ABAS (1.4 g, 5.14 mmole) was achieved in a similar fashion to Example 2, step 5. Purification by RPHPLC and lyophilization gave white solids (0.23 g). $^1$H NMR (d$_6$-DMSO) δ 2.5 (m, 5H), 2.9 (m, 1H), 4.6 (m, 1H), 5.1 (m, 1H), 5.4 (m, 2H), 5.8 (m, 1H), 7.7 (s, 4H), 8.4 (d, 1H), 9.2(s, 4H), 10.4 (s, 1H). MS (FAB) 345.2 (M+H+). Elemental Analysis: Calculated for $C_{19}H_{21}F_3N_4O_6.H_2O$: C 47.86 H 4.65 N 11.76; Found: C 48.15 H 4.41 N 11.24.

Step 5. Preparation of 3S-[[4-[[4-(aminoiminomethyl) phenyl]amino]-1,4-dioxobutyl]amino]-4-hydroxy-hex-5-enoic acid, trifluoroacetate Hydrolysis of the lactone prepared in step 4 was carried out as described in Example 2, step 6 using lithium hydroxide to give the desired hydroxy-acid lithium salt: MS(FAB) 363.2 (M+H+). Elemental Analysis: Calcd for $C_{17}H_{21}N_4O_5Li.1.5F_3C_2O_2H.2H_2O$: C 41.52 H 4.33 N 9.69; Found: C 42.96 H 4.13 N 9.25.

EXAMPLE 8

N-[4-(aminoiminomethyl)phenyl]-N'-[3,4-dihydro-2-oxo-2H-1-benzopyran-4-yl]butanediamide, Trifluoroacetate

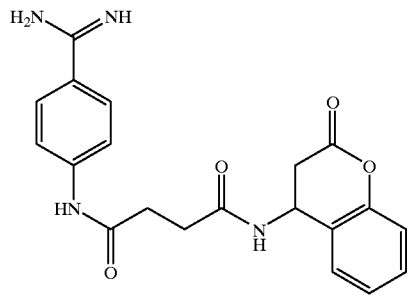

Step 1. Preparation of 3-[[4-[[4-(aminoiminomethyl) phenyl]-amino]-1,4-dioxobutyl]amino-]-3(-hydroxyphenyl) propanoic acid 4-[[4-(aminoiminomethyl)phenyl]-amino]-4-oxobutanoic acid hydrochloride prepared in Example 11 (4.6 g, 17 mmol) was added to dry DMF (225 ml) followed by N-methylmorpholine (1.2 g, 17 mmol) and isobutyl chloroformate (2.3 g, 17 mmol) at 25° C. The mixture was stirred for 5 min. Amino coumarin (3.4 g, 17 mmol) was added followed by triethylamine (1.8 g, 18 mmol) and catalytic dimethylaminopyridine. After 1 hour the solvent was removed under reduced pressure and the product purified by reverse phase chromatography (water/acetonitrile) to result in 3.5 g of a white solid: $^1$H NMR (d$_6$-DMSO) δ 2.53 (m, 2H), 2.65 (m, 2H) 2.87 (m, 2H), 3.07 (m, 2H), 5.40 (m, 1H), 7.14 (m, 2H), 7.35 (m, 2H), 7.79 (s, 4H), 8.28 (d, 1H, J=8.09 Hz), 8.92 (bs, 2H), 9.17 (bs, 2H), 10.44 (s, 1H); MS (FAB) m/e 399.1 (M+H+)—Elemental Analysis: Required for $C_{20}H_{22}N_4O_5.F_3C_2O_2H.H_2O$: C 48.72 H 4.56 N 10.21; Found: C 48.97 H 4.82 N 10.39.

Step 2. Preparation of N-[4-(aminoiminomethyl)phenyl]-N'-[3,4-dihydro-2-oxo-2H-1-benzopyran-4-yl]butanediamide, trifluoroacetate.

The product isolated in Example 8, step 1, (2.1 g, 5.5 mmol) was added to dry dioxane (20 ml) followed by addition of dry HCl/dioxane (10 ml) and stirred for 2–4 hr at 25° C. After this time the solvent was removed under reduced pressure and the product purified by reverse phase chromatography (water/acetonitrile) to result in 1.7 g of a white solid: $^1$H NMR (d$_6$-DMSO) δ 2.53 (m, 2H), 2.65 (m, 2H) 2.87 (m, 2H), 3.07 (m, 2H), 5.18 (m, 1H), 7.14 (m, 2H), 7.35 (m, 2H), 7.79 (s, 4H), 8.58 (d, 1H, J=8.09 Hz), 9.1 (bs, 2H), 9.19 (bs, 2H), 10.42 (s, 1H); MS (FAB) m/e 381.1 (M+H+). Elemental Analysis: Required for $C_{20}H_{20}N_4O_4.F_3C_2O_2H.H_2O$: C 50.36 H 4.31 N 10.57; Found: C 50.67 H 4.60 N 10.75.

EXAMPLE 9

N-[4-(aminoiminomethyl)phenyl]-N'-[tetrahydro-5-oxo-2-[5-(1,3-benzodioxolyl)]-3S-furanyl] butanediamide, Trifluoroacetate; Diastereoisomer 1

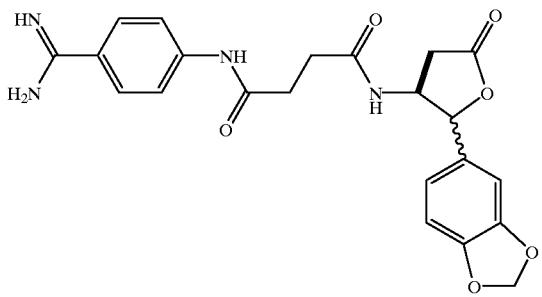

Step 1. Preparation of 1,3-benzodioxole-5-magnesium bromide.

To 1.74 g (0.072 mole) freshly-ground magnesium in 100 mL dry THF in a 250 mL round bottom flask was added in a dropwise fashion 13.1 g (0.062 mole) 4-bromo-1,2-(methylenedioxy)benzene in 50 mL dry THF. The reaction mixture was sonicated during the addition and the reaction temperature maintained below 50° C. by use of a water bath. Upon completion of reaction the mixture was filtered and used in the next step.

Step 2. Preparation of 3-N-tBoc-amino-4-hydroxy-4-[5-[1,3-(benzodioxolyl)]]-(3S)-butyric acid benzyl ester.

The aldehyde (5.58 g, 0.0182 mole) prepared in Example 2, Step 1 was reacted with the Grignard reagent prepared in Step 1 above (0.055 mole, 3 equiv.) using the procedure of Example 2, Step 2 to give the desired N protected hydroxy ester which was deemed sufficiently pure by NMR analysis to carry forward to the nest reaction without further purification. $^1$H NMR (300 MHz) δ 1.4 (m, 9H), 2.3 (m, 2H), 5.1 (m, 2H), 5.9 (m, 2H), 6.8 (m, 3H), 6.9 (s, 5H). MS FAB: 436.3 (M+Li).

Step 3. Preparation of 3-N-tBoc-amino-2-[5-[1,3-(benzodioxolyl)]]-5-oxo-(3S)-furane.

The hydroxy-acid ester obtained in Step 2 was converted to the lactone using the conditions given in Example 2, step 3. MS (FAB) 330.1 (M+H) 312 (M+H–H$_2$O).

Step 4. Preparation of Amino-4-[5-[1,3-benzodioxolyl)]]-5-oxo(3S)-furane.

The lactone prepared in Step 3 was deprotected as in Example 2, step 4 to give the desired amine hydrochloride salt. MS (FAB) 222 (M+H).

Step 5. Preparation of N-[4-(aminoiminomethyl)phenyl]-N'-[tetrahydro-5-oxo-2-[5-(1,3-benzodioxolyl)]-3S-furanyl] butanediamide, trifluoroacetate; diastereoisomer 1.

The coupling between the amino-lactone (1.60 g, 6.2 mmol) prepared in step 4 and ABAS (1.2 g, 4.4 mmol) was achieved in a similar fashion to Example 2, step 5. Purification by preparative RPHPLC and lyophilization of the two diastereoisomers A (0.22 g) and B (0.20 g) gave white solids. $^1$H NMR (300 MHz), (d$^6$-DMSO+TFA) δ: Isomer A; 2.6 (m, 6H), 4.8 (m, 1H), 5.6 (m, 1H), 6.0 (m, 2H), 6.8 (m, 3H), 7.8 (s, 4H), 8.2 (d, 1H), 9.0 (4H), 10.4 (s, 1H). MS (FAB) 439 (M+H). Elemental Analysis: Calculated for: $C_{22}H_{22}N_4O_6 \cdot C_2F_3O_2H \cdot 1.5H_2O$: C 49.74 H 4.49 N 9.67; Found: C 49.47 H 3.97 N 9.53.

Step 6. Preparation of 3S-[[4-[[4-(aminoiminomethyl) phenyl]amino]-1,4-dioxobutyl]amino]-4-hydroxy-[5-(1,3-benzodioxolyl)]butanoic acid, trifluoroacetate.

Hydrolysis of the lactone isolated in Step 5 (isomer A) was carried out as described in Example 2, step 6 to give the desired respective hydroxy acid anions. MS (FAB) 457.3 (M+H). Elemental Analysis: Calculated for $C_{22}H_{23}N_4O_7 \cdot 1.6$ $C_2F_3O_2H \cdot 1.6$ $Li \cdot H_2O$: C 45.36 H 3.90 N 8.40; Found: C 45.39 H 4.05 N 8.71.

EXAMPLE 10

N-[4-(aminoiminomethyl)phenyl]-N'-[tetrahydro-5-oxo-2-[5-(1,3-benzodioxolyl)-3S-furanyl] butanediamide, Trifluoroacetate; Diastereoisomer 2

Step 1. Preparation of N-[4-(aminoiminomethyl)phenyl]-N'-[tetrahydro-5-oxo-2-[5-(1,3-benzodioxolyl)-3S-furanyl] butanediamide trifluoroacetate.

This diastereoisomer was obtained as described in Example 9, step 5 as a white powder (0.2 g): $^1$H NMR (300 MHz) (d$_6$-DMSO+TFA), δ 2.7 (m, 6H), 4.4 (m, 1H), 5.2 (m, 2H), 6.0 (s, 2H), 6.8 (s, 2H), 7.0 (s, 1H), 7.8 (s, 4H), 8.5 (d, 1 H), 9.0 (m, 4H), 10.4 (s, 1 H). MS (FAB) 439 (M+H). Elemental analysis: Calcd. for $C_{22}H_{22}N_4O_6 \cdot 0.25C_2F_3O_2H \cdot 0.25$ $Li \cdot 0.5H_2$: C 49.73 H 4.06 N 9.47; Found: C 49.31 H 3.88 N 9.56.

Step 2. Preparation of 3S-[[4-[[4-(aminoiminomethyl) phenyl]amino]-1,4-dioxobutyl]amino-4-hydroxy-4-[5-(1,3-benzodioxolyl)]butanoic acid, trifluoroacetate.

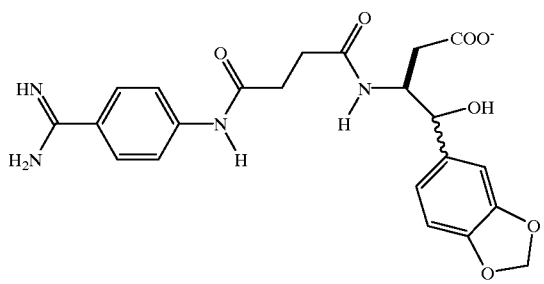

Hydrolysis of the lactone isolated in step 1 was carried out as described in Example 2, step 6 to give the desired respective hydroxy acid anions. MS (FAB) 457.3 (M+H). Elemental Analysis: Calcd. for $C_{22}H_{23}N_4O_7 \cdot 1.6C_2F_3O_2H \cdot 1.6Li \cdot H_2O$: C 45.36 H 3.90 N 8.40; Found: C 45.13 H 3.96 N 8.97.

EXAMPLE 11

Preparation of 4-[[4-(aminoiminomethyl)phenyl] amino]-4-oxo-butanoic Acid (ABAS)

Aminobenzamidine di-HCl (25 g, 120 mmol) was added to dry DMF (100 ml). To this solution dry pyridine (100 ml) and succinic anhydride (12 g, 120 mmol) followed by dimethylaminopyridine (DMAP, 1.5 g, 0.012 mmol) were added. The product precipitated after heating for ½ hour at 100° C. The product was filtered, washed with water, acetonitrile and ether. The white solid was suspended in dioxane, 4N HCl in dioxane (100 ml) was added and the suspension was stirred for 1 hour, filtered and dried in a desiccator to give 28 g, 88% of 4-[[4-(aminoiminomethyl) phenyl]amino]-4-oxo-butanoic acid as a white yellow solid which decomposes between 270 and 290° C.

Inhibition of Platelet Aggregation

The compounds of this invention are particularly useful for the inhibition of platelet aggregation and treatment of indications requiring inhibition or modulation of platelet aggregation.

In-Vitro Platelet Aggregation in PRP

Healthy male or female dogs were fasted for 8 hours prior to drawing blood; then 30 mL whole blood was collected using a butterfly needle and 30 mL plastic syringe with 3 mL of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature allowing the centrifuge to coast to a stop without braking. The PRP was removed from the blood with a plastic pipette and placed in a plastic-capped 50 mL Corning conical sterile centrifuge tube which was held at room temperature. Platelet-poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets/mL. The PRP preparation (400 μL) and 50 μL of the compound solution to be tested or saline were preincubated for 1 minute at 37° C. in a BioData aggregometer (BioData, Horsham, Pa.). Adenosine-5'-diphosphate (ADP, 50 μL, 50 μM final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The percent inhibition equals 100−(percent of control).

The compounds tested and their median inhibitory concentrations (IC$_{50}$) are recorded in Table 1. The IC$_{50}$ (dosage at which 50% of platelet aggregation is inhibited) were calculated by linear regression of the dose response curve. The assay results for the compounds of Examples 1 to 14 are also set forth in Table 1.

Inhibition of Ex Vivo Collagen-Induced Aggregation

The purpose of this assay is to determine the effects of antiplatelet compounds on ex vivo collagen-induced platelet aggregation when administered either intravenously or orally to dogs.

Pretreatment (control) blood samples are drawn from either conscious or anesthetized dogs (Beagles) and centrifuged to prepare platelet-rich plasma (PRP). Aggregatory response to collagen is measured in an aggregometer and used as a control. Compounds are administered, either intragastrically (either by capsule or stomach tube) or intravenously. Blood samples are drawn at predetermined intervals after compound administration, PRP is prepared and aggregation to collagen determined. Compound inhibition of aggregation is determined by comparing the aggregation response after compound administration to the pretreatment response.

TABLE 1

| Compound | | $IC_{50}$ | Ex Vivo Effect |
|---|---|---|---|
| Ex 1 | Step 4 | 3.0 | + |
| Ex 1 | Step 5 | 0.7 | NT |
| Ex 2 | Step 5 | 0.65 | + |
| Ex 2 | Step 6 | 1.6 | NT |
| Ex 3 | Step 1 | 2.5 | + |
| Ex 3 | Step 2 | 0.6 | NT |
| Ex 4 | Step 4 | 0.5 | — |
| Ex 4 | Step 5 | 0.15 | NT |
| Ex 5 | Step 2 | 0.8 | NT |
| Ex 6 | Step 6 | 0.45 | NT |
| Ex 7 | Step 5 | 0.29 | NT |
| Ex 8 | Step 1 | 0.26 | NT |
| Ex 8 | Step 2 | 0.2 | + |
| Ex 9 | Step 5 | 0.43 | NT |
| Ex 9 | Step 6 | 0.35 | NT |
| Ex 10 | Step 1 | 3.0 | NT |
| Ex 10 | Step 2 | 1.3 | NT |

What is claimed is:

1. A compound having the formula:

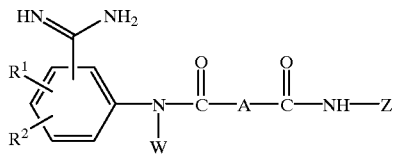

or a pharmaceutically acceptable salt thereof, wherein $R^1$ and $R^2$ are independently selected from the group consisting of hydrogen, halogen, alkoxy, alkyl hydroxy;

W is selected from the group consisting of hydrogen, alkyl, alkenyl, aryl or alkoxycarbonyl any of which may be substituted by alkyl, aryl or substituted aryl wherein each aryl substituent is selected from halo, alkoxy and alkyl;

A is selected from the group consisting of alkyl radicals, alkenyl radicals, alkynyl radicals, and alicyclic radicals, wherein each of said radicals may be optionally substituted with hydroxyl, alkoxy, alkyl, halo, aryl or substituted aryl, wherein the aryl substituent is selected from the group consisting of halo, nitro, alkoxy and alkyl;

Z is a lactone structure which is represented by the formula:

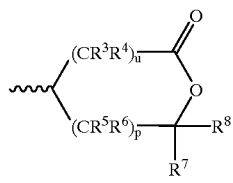

wherein $R^3$ and $R^4$ are independently selected from the group consisting of hydrogen, halo, alkoxy, alkyl and hydroxy;

$R^5$, $R^6$, $R^7$ and $R^8$ are independently selected from the group consisting of hydrogen, alkoxy, alkyl, alkenyl, alkyl sulfonyl, aryl sulfonyl; phosphate, phosphinate, phosphonate, each of which is attached through phosphorus and may be substituted on one or more of its oxygen atoms by alkyl, aryl, alkenyl or hydrogen; heterocyclic, phenyl, and substituted phenyl wherein each phenyl substituent is selected from halo, alkoxy, and alkyl;

u is an integer form 1 to 2;

p is an integer form 0 to 2; or

Z is a lactone which is fused to a benzene ring and represented by the formula

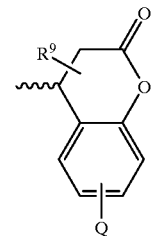

wherein Q is one or more substituents of the benzene ring which may be in any positions and are selected from the group consisting of hydrogen, halo, hydroxy, alkyl and alkoxy, and $R^9$ is selected from the group consisting of hydrogen, halo, carboxyl, alkoxycarbonyl, alkyl or alkoxy.

2. The compound of claim 1, wherein Z is

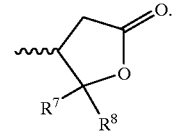

3. The compound of claim 1, wherein Z is

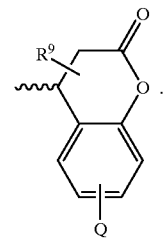

4. The compound of claims 2 or 3, wherein $R^1$ and $R^2$ are hydrogen.

5. The compound of claim 4, wherein W is hydrogen.

6. The compound of claim 5, wherein A is —$(CH_2)_2$—.

7. A compound according to claim 1 which is N-[4-(aminoiminomethyl)phenyl]-N'-(tetrahydro-5-oxo-3S-furanyl)butanediamide, trifluoroacetate.

8. A compound according to claim 1 which is N-[4-(aminoiminomethyl)phenyl]-N'-(tetrahydro-5-oxo-2-phenyl-3S-furanyl)butanediamide, trifluoroacetate.

9. A compound according to claim 1 which is N-[4-(aminoiminomethyl)phenyl-N'-[2R(S)-4-fluorophenyl)-tetrahydro-5-oxo-3S-furanyl]butanediamide, trifluoroacetate.

10. A compound according to claim 1 which is N-[4-(aminoiminomethyl)phenyl]-N'-[tetrahydro-5-oxo-2-(2-thiazolyl)-3S-furanyl]butanediamide, trifluoroacetate.

11. A compound according to claim 1 which is N-[4-(aminoiminomethyl)phenyl]-N'-[2-ethenyltetrahydro-5-oxo-3S-furanyl]butanediamide, trifluoroacetate.

12. A compound according to claim 1 which is N-[4-(aminoiminomethyl)phenyl]-N'-[3,4-dihydro-2-oxo-2H-1-benzopyran-4-yl]butanediamide, trifluoroacetate.

13. A compound according to claim 1 which is N-[4-(aminoiminomethyl)phenyl]-N'-[tetrahydro-5-oxo-2-[5(1,3-benzodioxolyl)-3S-furanyl]butanediamide, trifluoroacetate.

14. A pharmaceutical composition comprising at least one non-toxic pharmaceutically acceptable carrier and at least one compound according to any of claims 1–13.

15. A method of treating a mammal in need of platelet aggregation inhibition treatment comprising administering a therapeutically effective amount of the compound of any of claims 1–13 to the mammal.

* * * * *

UNITED STATES PATENT AND TRADEMARK OFFICE
CERTIFICATE OF CORRECTION

PATENT NO. : 6,037,365
DATED : March 14, 2000
INVENTOR(S) : Philippe Roger Bovy et al.

It is certified that error appears in the above-identified patent and that said Letters Patent is hereby corrected as shown below:

Title page,
Item [56] References Cited, OTHER PUBLICATIONS
After "M. Taddei et al.," "peroxxide" should read -- peroxide --.

Column 1,
Line 48, "35" should be deleted.

Column 6,
Line 17, "sucrose" should read -- sucrose, --.

Column 10,
Line 52, "examethyldisilazane" should read -- hexamethyldisilazane --;
Line 53, "enzylamide" should read -- benzylamide --.

Column 13,
Line 52, "[ ( TMSO ) 2]," should read -- [ ( TMSO )$_2$ ], --.

Column 16,
Line 31, "Trifluoroacetate" should read -- trifluoroacetate --;
Line 51, "(? g, 41.4" should read -- (41.4 --.

Column 17,
Line 29, "1OH);" should read -- 1OH); --.

Column 18,
Line 17, "Trifluoroacetate" should read -- trifluoroacetate --;
Line 63, $C_{21}$, $H_{21}FN_4O_4 \cdot C2F_3O_2 \cdot H_2O$" should read -- $C_{21}H_{21}FN_4O_4 \cdot C_2F_3O_2 \cdot H_2O$ --;
and "50.69" should read -- C 50.69 --.

Column 19,
Line 17, "7.39" should read -- 7.35 --;
Line 28, "$C_{21}H_{23}FN_4O_5$ $1.5F_3C_2O_2LiH_2O$" should read -- $C_{21}H_{23}FN_4O_5$ $1.5F_3C_2O_2Li \cdot H_2O$ --.

UNITED STATES PATENT AND TRADEMARK OFFICE
CERTIFICATE OF CORRECTION

PATENT NO. : 6,037,365
DATED : March 14, 2000
INVENTOR(S) : Philippe Roger Bovy et al.

It is certified that error appears in the above-identified patent and that said Letters Patent is hereby corrected as shown below:

Column 22,
Line 57, "nest" should read -- next --.

Signed and Sealed this

Twenty-third Day of October, 2001

*Attest:*

NICHOLAS P. GODICI
*Attesting Officer*   *Acting Director of the United States Patent and Trademark Office*